United States Patent [19]

Smith

[11] 4,010,171
[45] Mar. 1, 1977

[54] PROCESS FOR PREPARING TETRAHYDROFURAN

[75] Inventor: William Edward Smith, Schenectady, N.Y.

[73] Assignee: General Electric Company, Pittsfield, Mass.

[22] Filed: Oct. 20, 1975

[21] Appl. No.: 623,905

Related U.S. Application Data

[63] Continuation-in-part of Ser. No. 420,853, Dec. 3, 1973, abandoned.

[52] U.S. Cl. .................................. 260/346.1 R
[51] Int. Cl.$^2$ .................................. C07D 307/08
[58] Field of Search .......................... 260/346.1 R

[56] References Cited

FOREIGN PATENTS OR APPLICATIONS 1,170,222  11/1969  United Kingdom ........ 260/346.1 R

*Primary Examiner*—Henry R. Jiles
*Assistant Examiner*—Bernard Dentz
*Attorney, Agent, or Firm*—Donald M. Papuga; William F. Mufatti

[57] ABSTRACT

A process for preparing tetrahydrofuran which comprises heating a carboxylic acid diester of 1,4-butanediol in the vapor phase in the presence of water and a hydrolysis-dehydroacyloxylation catalyst.

3 Claims, No Drawings

PROCESS FOR PREPARING TETRAHYDROFURAN

This application is a continuation-in-part application of Patent Application Ser. No. 420,853, filed Dec. 3, 1973, and now abandoned.

This invention relates to a process for preparing tetrahydrofuran which comprises heating a carboxylic acid diester of 1,4-butanediol in the vapor phase in the presence of water and a hydrolysis-dehydroacyloxylation catalyst.

BACKGROUND OF THE INVENTION

It is known in the art that tetrahydrofuran may be produced by a number of different methods, the more prominent among them the dehydration of 1,4-butanediol and the catalytic hydrogenation of furan. Most tetrahydrofuran is, in fact, manufactured in a multi-step sequence starting with the reaction of acetylene and formaldehyde in the presence of a cuprous acetylide complex to form butynediol. The butynediol is hydrogenated to butanediol, which is dehydrated to tetrahydrofuran as indicated above.

In addition, tetrahydrofuran can be prepared by catalytic hydrogenation of maleic, fumaric and succinic acids, their respective anhydrides and ester derivatives, and butyrolactone.

All of these methods involve the use of hazardous or expensive materials, and catalysts that are expensive in some instances and easily poisoned in others.

The liquid phase conversion of 1,4-butanediol carboxylate ester derivatives to tetrahydrofuran in the presence of strongly acidic catalysts and water has been described by Kohll in British Patent 1,170,222 and by Ono et al in German Offenlengungsschrift 2,062,950. These processes are characterized by low rates and extent of conversion.

Tetrahydrofuran is a useful solvent for natural and synthetic resins and is a valuable intermediate in manufacture of a number of chemicals and plastics.

DESCRIPTION OF THE INVENTION

It has been discovered that tetrahydrofuran may be advantageously prepared by heating a carboxylic acid diester of 1,4-butanediol in the vapor phase in the presence of water and a heterogeneous hydrolysis-dehydroacyloxylation catalyst. The method is characterized by high reaction efficiency; yields are essentially quantitative and a high conversion of the starting ester may be accomplished per pass. In addition, the method is applicable to conversion of 1,4-butanediol diacetate used in admixture with 4-acetoxybutanol and 1,4-butanediol and the corresponding diacetates, monoacetates and free diols of the isomeric 1,2-butanediol and 2-methyl-1,3-propanediol systems.

The process is illustrated for the case of 1,4-butanediol diacetate in Equation 1.

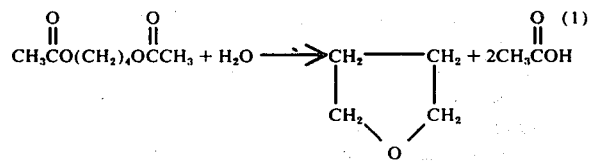

The above transformation is actually the net result of two consecutive reactions represented by the following equations:

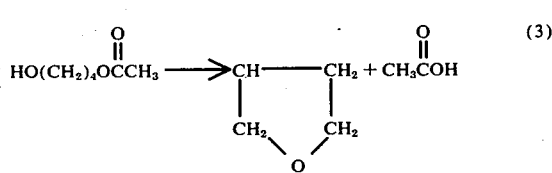

A class of hydrolysis-dehydroacyloxylation catalysts particularly effective in promoting the ring closure and evolution of the carboxylic acid includes alumina, silica, silica-alumina, silica-magnesia, and other combinations in which either silica or alumina or their combination constitute the principal component. The silica-alumina hydrolysis-dehydroacyloxylation catalysts which may be used vary in composition from pure silica to pure alumina whereas the silica-magnesias vary in composition from pure silica to predominantly magnesia. The catalysts of the instant invention do not include those activated by treatment with strong acid. Such catalysts when used in the disclosed process promote undesired side reactions and, in addition, rapidly lose their activity and physical integrity.

The carboxylic acid diesters of 1,4-butanediol suitable for use in the disclosed process are those in which the carboxy function contains from one to six carbon atoms. A preferred diester is 1,4-butanediol diacetate. In a preferred embodiment, the 1,4-butanediol diacetate is used in admixture with 1,4-butanediol, 4-acetoxybutanol and the corresponding monoacetate, diol and diacetate derivatives of 1,2-butanediol and 2-methyl-1,3-propanediol. As disclosed in copending application Ser. No. 581,266, filed on May 27, 1975, entitled A *Process for Preparing Tetrahydrofuran* and assigned to the same assignee as the present invention, such a mixture can be derived from propylene by way of allyl acetate and a hydroformylation-hydrogenation sequence.

The process is carried out in the presence of water, in which case the diacetate present undergoes hydrolysis to the monoacetate which subsequently is converted to tetrahydrofuran and acetic acid. Thus, at least one mole of water is required for each mole of diacetate to be converted. Generally, a ratio of from one to 30 moles of water per mole of diacetate is sufficient to effect the desired conversion.

The temperature at which the disclosure process can be carried out varies from about 200° C to about 325° C. Preferably, the reaction is carried out in the temperature range of from about 200° C to about 270° C. The maximum depends upon destruction of the product, olefin formation occurring from the 1,4-derivatives under too rigorous conditions.

In a preferred embodiment, a mixture of which 1,4-butanediol diacetate and water are principal components is vaporized and passed through a fixed bed of the heated catalyst. The effluent is distilled to effect isolation of the tetrahydrofuran and acetic acid. Well-known techniques can be used to obtain the products in maximum yield and purity.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

Apparatus — A vertical hot tube reactor (16 mm ID × 70 cm effective length) is constructed from heavy wall glass, with 24/40 male and female joints. Vigreaux points are indented just above the male joint to support catalyst pellets. Thermocouple leads are fastened into three other Vigreaux indentations at points along the length. Three 4 ft. × 1 in. Briskheat glass insulated heating tapes are wound onto the tube, covered with glass wool and glass tape, and connected to separate variable transformers. The tube exit is connected by a gooseneck (also heated) to an efficient condenser and collection vessel. A three necked flask serves as the evaporator, with the reactants added from addition funnels in side necks. Nitrogen carrier gas is passed through to provide residence times on the order of 3 to 10 seconds.

EXAMPLE 1

The tube reactor described above is charged with 89 grams of silica-alumina catalyst (87% silica — 13% alumina, 3/16 inch × 3/16 inch pills, Davison Chemical Grade 970) and is maintained at 220°–250° C while 50.0 grams of 1,4-butanediol diacetate and 50 ml. of water, admitted to the evaporator simultaneously from separate addition funnels, are copassed through over a one hour period. Quantitative glpc analysis (propionic acid internal standard) of the effluent shows the presence of 9.0 grams of 1,4-butanediol diacetate (18% recovery), 16.3 grams of tetrahydrofuran (96% yield based on 82% conversion), and 28.2 grams of acetic acid (100% yield based on 82% conversion). No butanediol or butanediol monoacetate is detected.

On distillation, the tetrahydrofuran-water azeotrope is easily separated, leaving a water-acetic acid-butanediol diacetate residue which can be further distilled to afford materials for recycle.

EXAMPLE 2

The tube reactor is charged with 85 grams of silica-magnesia catalyst (70% silica — 30% magnesia, 3/16 inch × 3/16 inch pills, Davison Chemical) and maintained at 220°–250° C. As in Example 1, 50.0 grams of 1,4-butanediol diacetate and 50 ml. of water are copassed over one hour. The effluent contains, as shown by quantitative glpc analysis, 12.2 grams of the unconverted butanediol diacetate (24% recovery), 15.1 grams of tetrahydrofuran and 24.4 grams of acetic acid (96% and 93% yields, respectively, based on 76% conversion), and 0.1 grams of 4-acetoxybutanol (0.3% yield).

EXAMPLE 3

The tube reactor, charged with 110 grams of alumina catalyst (⅛ inch pellets, Harshaw Al-0104T), is maintained at 250° C while 25.0 grams of 1,4-butanediol diacetate and 50 ml. of water are admitted to the evaporator simultaneously from different addition funnels over a 20 minute period. The aqueous effluent collected contains tetrahydrofuran, acetic acid, and about 10% of the original diacetate. The mixture is again taken through the tube. The effluent from this second pass contains, as found by quantitative glpc analysis, 0.3 grams of residual butanediol diacetate (1% unconverted), 9.2 grams of tetrahydrofuran (90% yield), and 15.9 grams of acetic acid (93% yield).

EXAMPLE 4

A 50.0 gram mixture containing 31.7 grams of 4-acetoxybutanol, 10.2 grams of 1,4-butanediol diacetate, a very small amount of 1,4-butanediol, and oxo by-products (about 6 grams of acetate derivatives of 2-methyl-1,3-propanediol and 1,2-butanediol) is copassed with 50 ml. of water through the tube reactor and alumina catalyst described in Example 3, at 250°–270° C. over a 1-hour period. A glpc analysis of the effluent shows the presence of tetrahydrofuran, acetic acid and a few other minor components, but no 1,4-butanediol derivatives. The product mixture is distilled through a 300 mm. Vigreaux column. The first 54 grams taken off (boiling over the 64°–100° C. range) contains, as shown by quantitative glpc analysis, all of the tetrahydrofuran formed — 20.4 grams, corresponding to a 95% yield based on conversion of all 1,4-butanediol monoacetate and diacetate initially present. Analysis of the total distillate shows the presence of 24.3 grams of acetic acid.

EXAMPLE 5

A mixture of completely acetylated oxo acetates composed of 37.8 grams of 1,4-butanediol diacetate, 4.7 grams of 2-methyl-1,3-propanediol diacetate and 7.5 grams of 1,2-butanediol diacetate is copassed with 50 ml. of water through the tube and the silica-alumina catalyst described in Example 1, at 220°–250° C., over a one-hour period. Quantitative glpc analysis of the effluent indicates the presence of 4.9 grams of the 1,4-butanediol diacetate (13% unconverted), 12.9 grams of tetrahydrofuran (95% yield based on 87% conversion), 29.1 grams of acetic acid, and small quantities of the byproduct diols (2-methyl-1,3-propanediol and 1,2-butanediol) and their various acetate derivatives and olefinic decomposition products.

EXAMPLE 6

This example is included to demonstrate the deleterious effect of using the subject catalysts modified by treatment with strong acid.

The tube reactor is charged with a catalyst prepared by impregnating the silica-alumina described in Example 1 with 10% by weight of sulfuric acid. After calcining at 400°, the catalyst bed is maintained at 220° C while the feedstock described in Example 1 is passed into the boiler. The initial level of conversion is about the same as with the unmodified catalyst. The activity rapidly falls off, however, and in addition the pellets darken and disintegrate.

It should, of course, be apparent to those skilled in the art that changes may be made in the particular embodiments of the invention described which are within the full intended scope of the invention as defined by the appended claims.

What is claimed is:

1. A process for preparing tetrahydrofuran which comprises heating a carboxylic acid diester of 1,4-butanediol in the vapor phase in the presence of water and a hydrolysis-dehydroacyloxylation catalyst selected from the group consisting of alumina, silica, silica-alumina, and silica-magnesia at a temperature in the range of from 200° C to about 325° C.

2. The process of claim 1 in which the carboxylic acid diester of 1,4-butanediol is the diacetate of 1,4-butanediol.

3. The process of claim 1 wherein the water is present in a ratio of from one to 30 moles of water per mole of the carboxylic acid diester of 1,4-butanediol.

* * * * *